(12) United States Patent
Kim et al.

(10) Patent No.: US 8,103,066 B2
(45) Date of Patent: Jan. 24, 2012

(54) ULTRASOUND SYSTEM AND METHOD FOR FORMING AN ULTRASOUND IMAGE

(75) Inventors: Tae Yun Kim, Seoul (KR); Jin Yong Lee, Seoul (KR)

(73) Assignee: Medison Co., Ltd., Hongchun-gun (KR)

( * ) Notice: Subject to any disclaimer, the term of this patent is extended or adjusted under 35 U.S.C. 154(b) by 976 days.

(21) Appl. No.: 11/770,351

(22) Filed: Jun. 28, 2007

(65) Prior Publication Data
US 2008/0044054 A1 Feb. 21, 2008

(30) Foreign Application Priority Data
Jun. 29, 2006 (KR) .................. 10-2006-0059121

(51) Int. Cl.
*G06K 9/00* (2006.01)
(52) U.S. Cl. .................. 382/128; 382/132; 600/437
(58) Field of Classification Search .................. 382/128, 382/132; 600/437, 443, 447; 378/37; 128/916
See application file for complete search history.

(56) References Cited

U.S. PATENT DOCUMENTS

| | | | |
|---|---|---|---|
| 6,396,940 B1 * | 5/2002 | Carrott et al. .................. | 382/128 |
| 6,464,642 B1 * | 10/2002 | Kawagishi .................. | 600/454 |
| 6,468,218 B1 * | 10/2002 | Chen et al. .................. | 600/443 |
| 6,567,549 B1 * | 5/2003 | Marianetti et al. .................. | 382/189 |
| 6,671,539 B2 * | 12/2003 | Gateno et al. .................. | 600/426 |
| 6,714,667 B1 * | 3/2004 | Mooney et al. .................. | 382/128 |
| 6,846,289 B2 * | 1/2005 | Besson et al. .................. | 600/437 |
| 6,970,587 B1 * | 11/2005 | Rogers .................. | 382/132 |
| 7,046,860 B2 * | 5/2006 | Soubelet et al. .................. | 382/294 |
| 7,103,205 B2 * | 9/2006 | Wang et al. .................. | 382/132 |
| 7,336,804 B2 * | 2/2008 | Steffin .................. | 382/104 |
| 7,358,965 B2 * | 4/2008 | Barabe et al. .................. | 345/179 |
| 7,507,204 B2 * | 3/2009 | Shim et al. .................. | 600/443 |
| 7,611,466 B2 * | 11/2009 | Chalana et al. .................. | 600/443 |
| 8,031,923 B2 * | 10/2011 | Schummers et al. .................. | 382/128 |
| 2002/0126884 A1 * | 9/2002 | Gerritsen et al. .................. | 382/131 |

(Continued)

FOREIGN PATENT DOCUMENTS
EP 1 523 939 A1 4/2005
(Continued)

OTHER PUBLICATIONS

Hein et al. "Three Dimensional Blood Flow Velocity Vector Estimation With a Triple Beam Ultrasonic Lens" (1994) IEEE pp. 1-6.*

(Continued)

*Primary Examiner* — Jason M Repko
*Assistant Examiner* — Mia M Thomas
(74) *Attorney, Agent, or Firm* — Oblon, Spivak, McClelland, Maier & Neustadt, L.L.P.

(57) ABSTRACT

The ultrasound system includes a processor that extracts plane data from volume data formed by using ultrasound signals received from a target object to form a plane image and sets a region of interest (ROI) on the plane image. The processor extracts at least a portion of the volume data to form a ROI image and a 3D image corresponding to the ROI image. A control unit controls a display unit to display the plane image together with the 3D image, and also controls the processor to set a new ROI on the displayed plane image to form a new ROI image and a 3D image corresponding to the new ROI image.

7 Claims, 7 Drawing Sheets

U.S. PATENT DOCUMENTS

| | | | |
|---|---|---|---|
| 2002/0145941 A1* | 10/2002 | Poland et al. | 367/11 |
| 2003/0099391 A1* | 5/2003 | Bansal et al. | 382/131 |
| 2003/0103665 A1* | 6/2003 | Uppaluri et al. | 382/131 |
| 2004/0081340 A1* | 4/2004 | Hashimoto | 382/128 |
| 2004/0127794 A1* | 7/2004 | Murashita | 600/442 |
| 2004/0193053 A1* | 9/2004 | Kato | 600/440 |
| 2004/0213445 A1* | 10/2004 | Lee et al. | 382/128 |
| 2004/0249270 A1* | 12/2004 | Kondo et al. | 600/425 |
| 2005/0101863 A1* | 5/2005 | Kawagishi et al. | 600/443 |
| 2005/0228250 A1* | 10/2005 | Bitter et al. | 600/407 |
| 2005/0267365 A1* | 12/2005 | Sokulin et al. | 600/437 |
| 2005/0267366 A1* | 12/2005 | Murashita et al. | 600/437 |
| 2006/0002631 A1* | 1/2006 | Fu et al. | 382/294 |
| 2006/0018548 A1* | 1/2006 | Chen et al. | 382/190 |
| 2006/0049358 A1* | 3/2006 | Oumi et al. | 250/370.08 |
| 2006/0058605 A1 | 3/2006 | Deischinger et al. | |
| 2006/0058651 A1* | 3/2006 | Chiao et al. | 600/437 |
| 2010/0185094 A1* | 7/2010 | Hamada et al. | 600/443 |
| 2011/0040168 A1* | 2/2011 | Arnaud et al. | 600/407 |

FOREIGN PATENT DOCUMENTS

| | | |
|---|---|---|
| JP | 2004-202132 | 7/2004 |
| JP | 2006-141509 | 6/2006 |
| JP | 2006-167100 | 6/2006 |
| KR | 10-2005-0097298 | 10/2005 |
| KR | 10-2006-0050433 | 5/2006 |
| WO | WO 2006/056614 A1 | 6/2006 |

OTHER PUBLICATIONS

Hein et al. "Three Dimensional Blood Flow Velocity Vector Estimation With Triple Beam Ultrasonic Lens" Bio Imaging Research IEEE 1994, pp. 1-6.*

* cited by examiner

ULTRASOUND SYSTEM AND METHOD FOR FORMING AN ULTRASOUND IMAGE

The present application claims priority from Korean Patent Application No. 10-2006-0059121 filed on Jun. 29, 2006, the entire subject matter of which is incorporated herein by reference.

BACKGROUND

1. Field

The present invention generally relates to an ultrasound system, and more particularly to an ultrasound system and a method for forming an ultrasound image.

2. Background

An ultrasound system has become an important and popular diagnostic tool since it has a wide range of applications. Specifically, due to its non-invasive and non-destructive nature, the ultrasound system has been extensively used in the medical profession. Modern high-performance ultrasound diagnostic systems and techniques are commonly used to produce two or three-dimensional (2D or 3D) ultrasound images of internal features of an object (e.g., human organs).

In terms of operation, the ultrasound system transmits ultrasound signals to the target object and then receives ultrasound echo signals. The ultrasound system forms volume data of the target object based on the received ultrasound echo signals. Upon input of plane selection information for selecting a specific plane from the volume data is inputted through an input unit, the ultrasound system extracts data corresponding to the selected plane from the volume data. The ultrasound system forms a plane image (2D image) based on the extracted data to be displayed through a display unit.

Subsequently, if region of interest (ROI) setting information is inputted through the input unit, the ultrasound system sets the ROI on the 2D image based on the ROI setting information. The ultrasound system extracts data corresponding to the ROI from the volume data and then renders the extracted data, thereby forming the 3D image. The 3D image is displayed together with the 2D image corresponding to ROI on the display unit.

In the user of the ultrasound system, a need may arise to reset the ROI for displaying 2D and 3D images corresponding to a different portion of the target object. If ROI reset information is received through the input unit, the ultrasound system resets the ROI on the 2D image based on the ROI reset information. For setting a new ROI, a display mode displaying the 2D image together with the 3D image should be changed to a single display mode because the ROI setting can be carried out only at the single display mode for displaying only one 2D image in the conventional ultrasound system. That is, a multi display mode for displaying the 3D image together with the 2D image should be changed to the single display mode. Therefore, since the display mode has to be changed to reset the ROI, there are problems that it is inconvenient to reset the ROI, and an amount of time needed for diagnosis increases.

BRIEF DESCRIPTION OF THE DRAWINGS

Arrangements and embodiments may be described in detail with reference to the following drawings in which like reference numerals refer to like elements and wherein.

DETAILED DESCRIPTION

Figure 1:
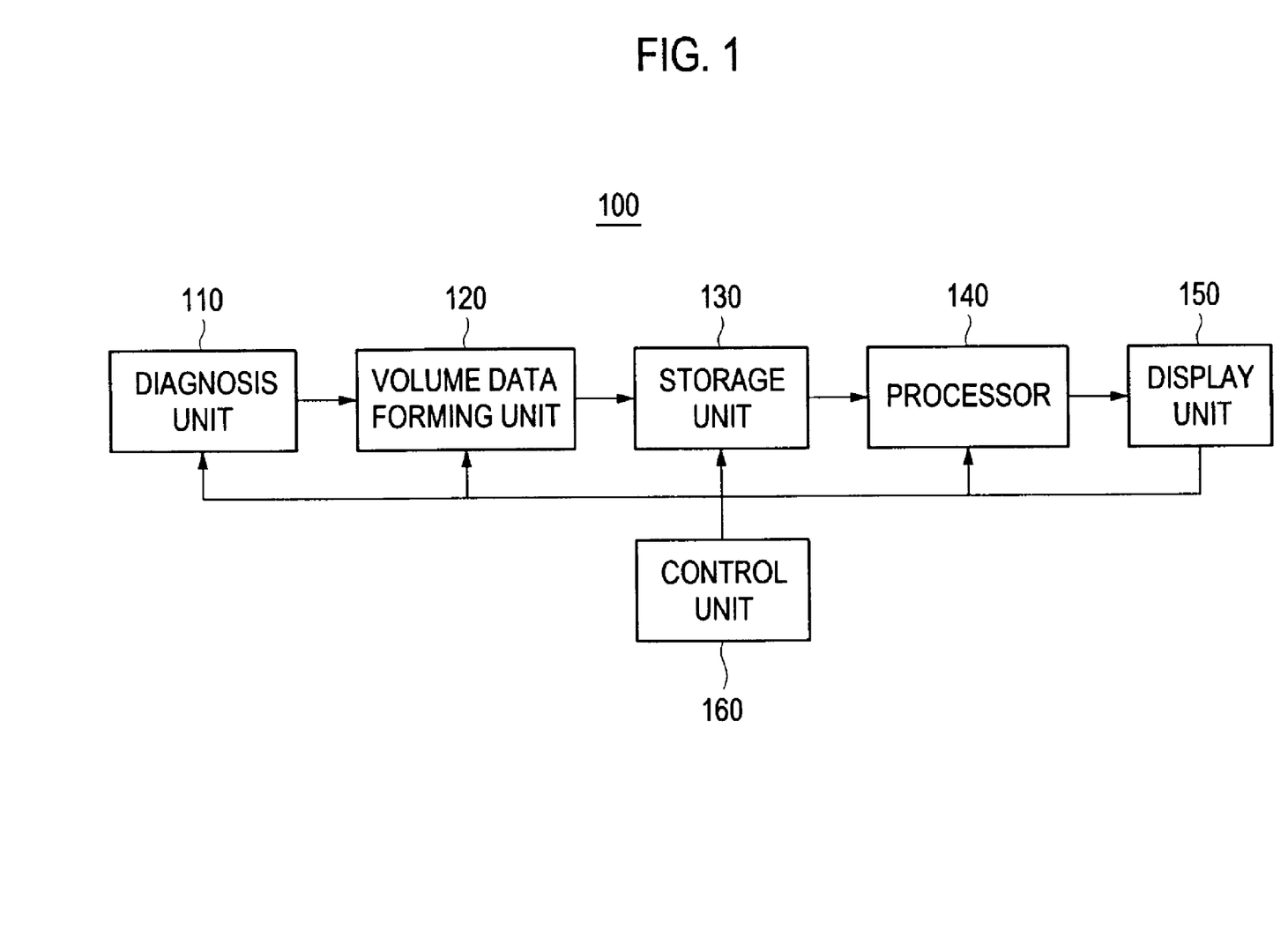
FIG. 1 is a schematic block diagram illustrating an ultrasound diagnostic device constructed in accordance with one embodiment of the present invention.

Hereinafter, the present invention will be described in detail with reference to following FIGS. 1 to 7. FIG. 1 is a block diagram illustrating an ultrasound system, which is constructed in accordance with the present invention. As shown in FIG. 1, the ultrasound system 100 includes a diagnosis unit 110, a volume data forming unit 120, a storing unit 130, a processor 140, a display unit 150 and a control unit 160. The ultrasound system 100 may further include an input unit (e.g., mouse, track ball, key board, touch pad, etc.) for receiving region of interest (ROI) setting information for setting a ROI from a user.

The diagnosis unit 110 includes a probe and a beam former (not shown). The probe contains a plurality of transducer elements for reciprocally converting electric signals and ultrasound signals. The probe transmits ultrasound signals to a target object and receives ultrasound echo signals reflected from the target object. The probe converts the received ultrasound echo signals into electric signals (Hereinafter, referred to as receive signals). The beam former applies delays to the receive signals, thereby producing focused receive signals.

The volume data forming unit 120 forms volume data based on the focused receive signals outputted from the diagnosis unit 110. The volume data may be stored in the storage unit 130.

Figure 3:
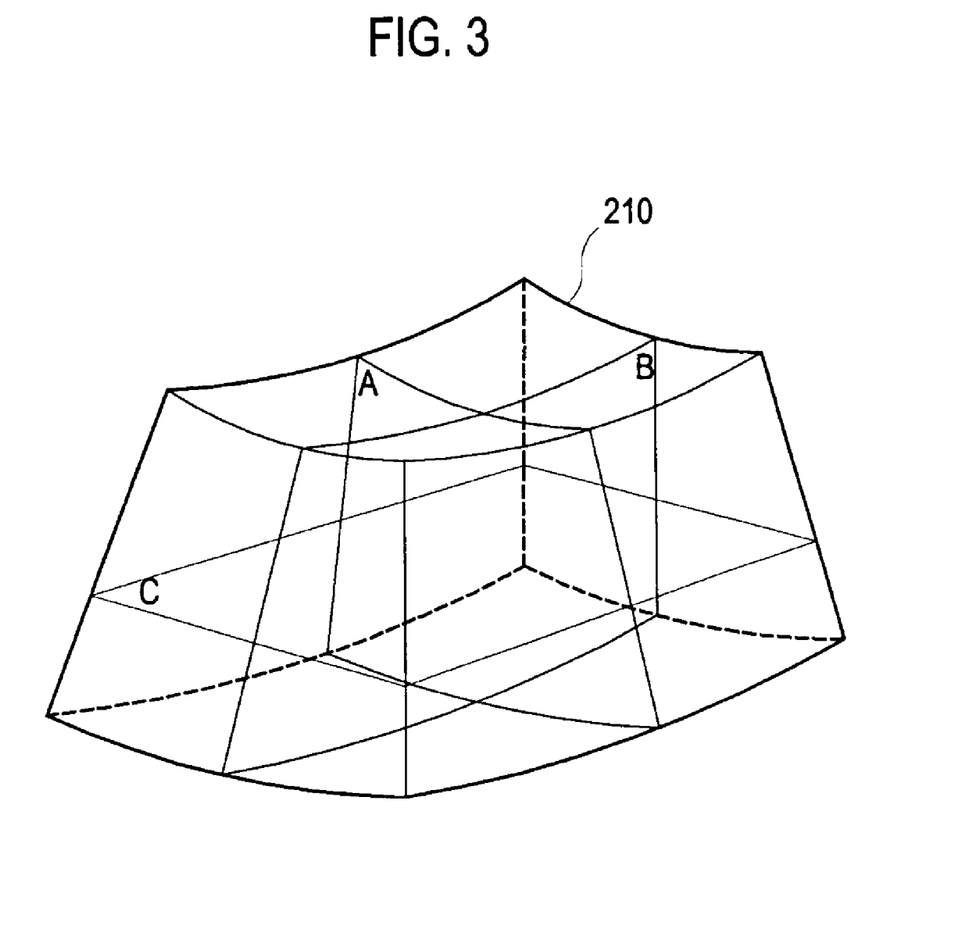
FIG. 3 is a schematic diagram showing an example of volume data and reference planes.

If reference plane selection information for selecting a reference plane is inputted from a user, the processor 140 extracts data corresponding to the selected reference plane from the volume data stored in the storage unit 130. The processor 140 performs image signal processing based on the extracted data to form an image signal corresponding to the selected reference plane. A reference plane image is formed based on the image signal. The reference plane may be one of A, B and C planes in the volume data 210 as shown in FIG. 3.

Figure 4:
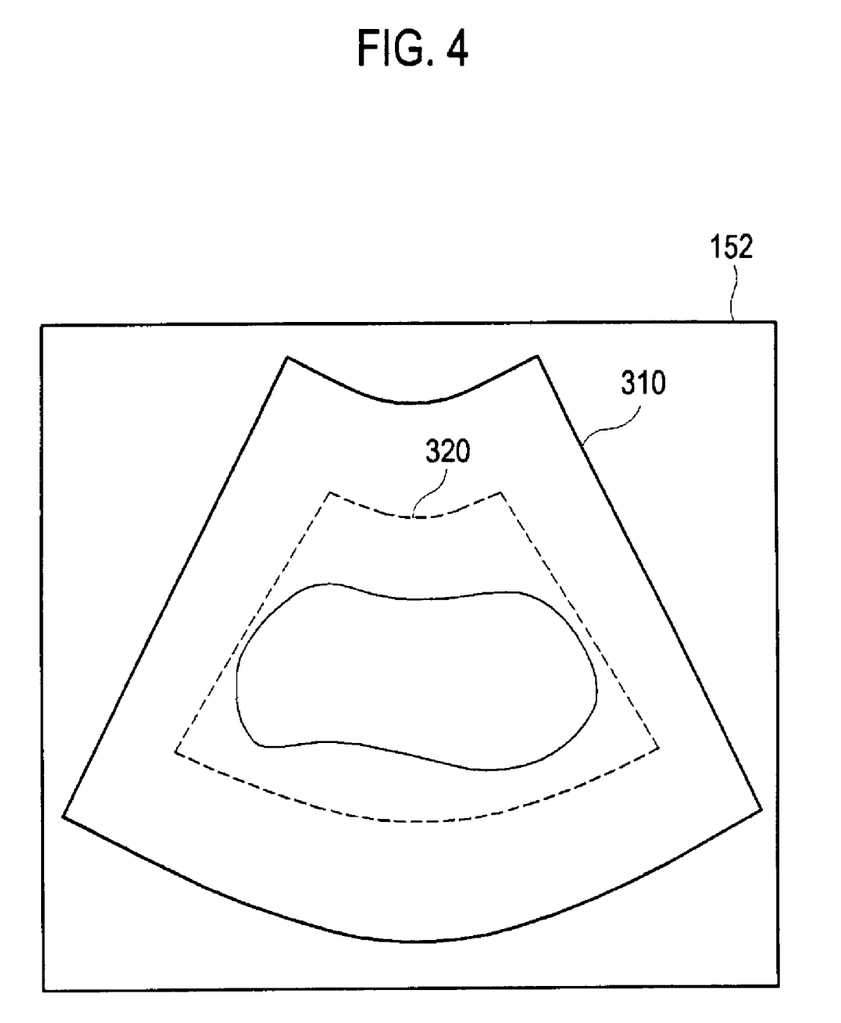
FIGS. 4 to 7 are diagrams showing examples of displaying ultrasound images in accordance with the present invention.

Subsequently, if ROI setting information is inputted through the input unit, the processor 140 sets ROI 320 on the reference plane image 310 as shown in FIG. 4 and then extracts data corresponding to the ROI 320 from the volume data. The processor 140 performs image signal processing based on the extracted data, thereby forming a ROI image signal and a 3D image signal corresponding to the ROI.

The display unit 150 receives the reference plane image signal, the ROI image signal and the 3D image signal to display the reference plane image, a ROI image and a 3D image on a display region. If a single display mode is selected in the ultrasound system, the display region is used to display one image. On the contrary, if a multi display mode is selected in the ultrasound system, the display region of the display 150 may be partitioned into a plurality of sub display regions, wherein each sub display region displays one of the reference plane image, the ROI image and the 3D image. For instance, the display region of the display unit 150 may be partitioned into a first sub display region and a second sub display region at the multi display mode. In this case, the ROI image may be displayed on the first sub display region and the 3D image may be displayed on the second sub display region.

The control unit 160 may control the processor 140 to extract the data corresponding to the ROI from the volume data stored in the storage unit 130 in response to the ROI setting information. The ROI setting information may include information associated with a size and a position of the ROI. Also, the control unit 160 may control the partitioning of the display region of the display unit 150 according to the display mode. Further, the control unit 160 may check whether ROI reset information is inputted through the input unit. If the ROI reset information is inputted, the control unit 160 controls the display unit 150 such that the reference plane image is displayed on the first sub display region instead of displaying the ROI image. Therefore, if new ROI setting information is inputted, the new ROI may be set on the reference plane image displayed on the first sub display region while the 3D image is displayed on the second sub display region.

Figure 2:
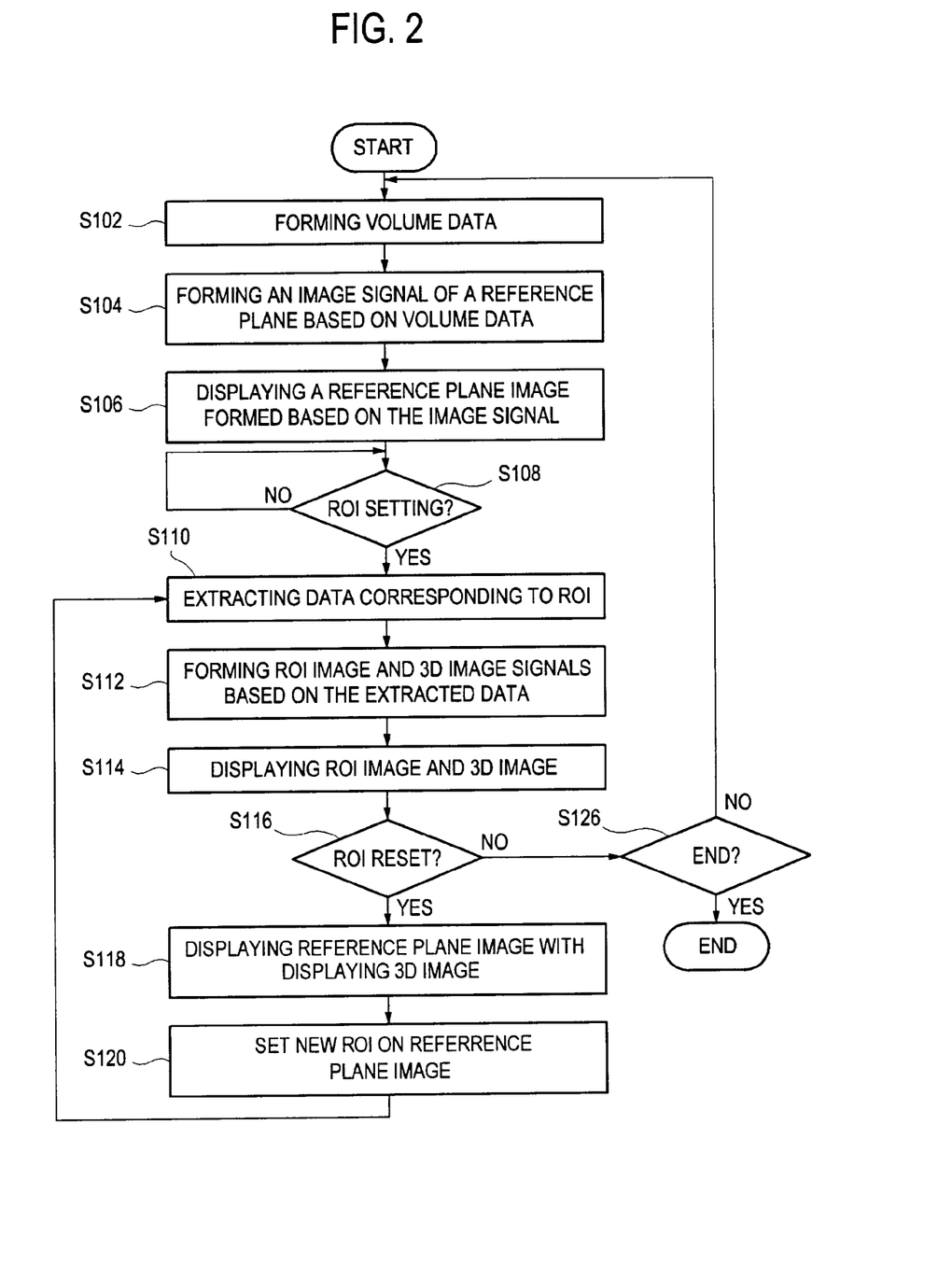
FIG. 2 is a flowchart illustrating a method of forming an ultrasound image in accordance with one embodiment of the present invention.

Hereinafter, a process for forming ultrasound images will be described in detail with reference to FIGS. 2 to 7. FIG. 2 is a flowchart showing a process for forming ultrasound images in accordance with one embodiment of the present invention.

As shown, the volume data forming unit 120 forms volume data based on ultrasound echo signals received at the diagnosis unit 110 and the volume data are stored in the storage unit as step S102. If reference selection information is inputted, the processor 140 extracts data corresponding to a reference planes selected based on the plane selection information from the volume data and then performs image signal processing based on the extracted data, thereby forming a reference plane image signal at step S104. The display unit 150 receives the reference plane image signal from the processor 140 to display a reference plane image 310 on a display region 152 as shown in FIG. 4 at step S106. The control unit 160 checks whether the ROI setting information is inputted through the input unit at step S108. If the ROI setting information is not inputted, the control unit 160 stands by until the ROI setting information is inputted.

Figure 5:
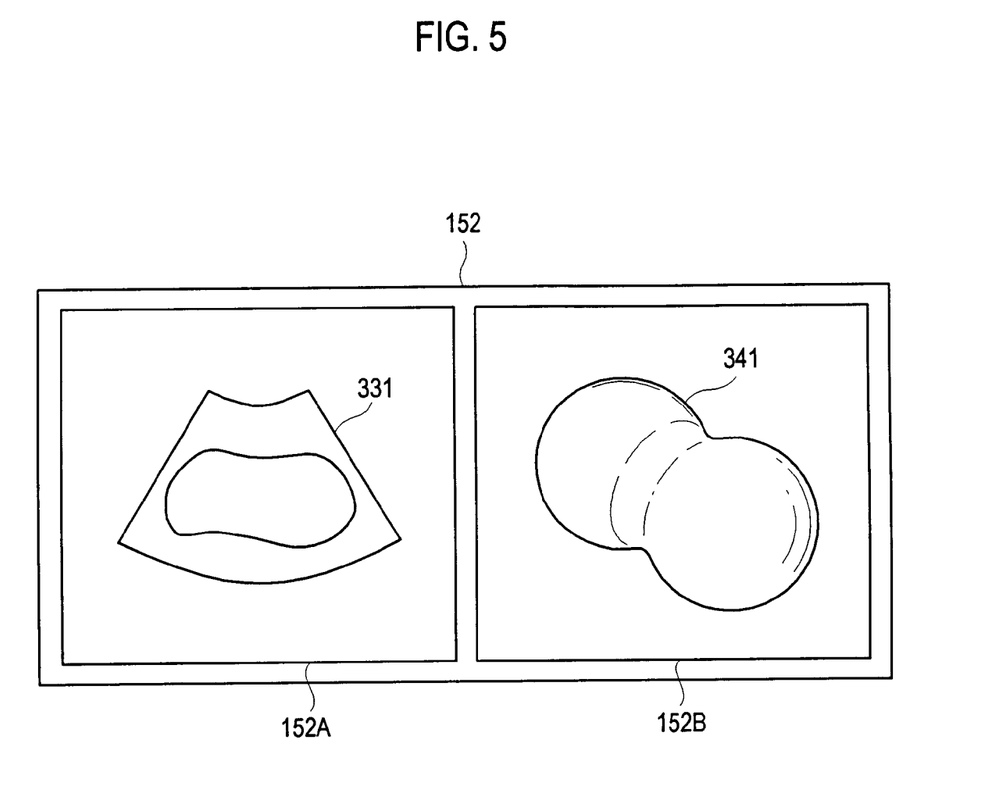
Figure 6:
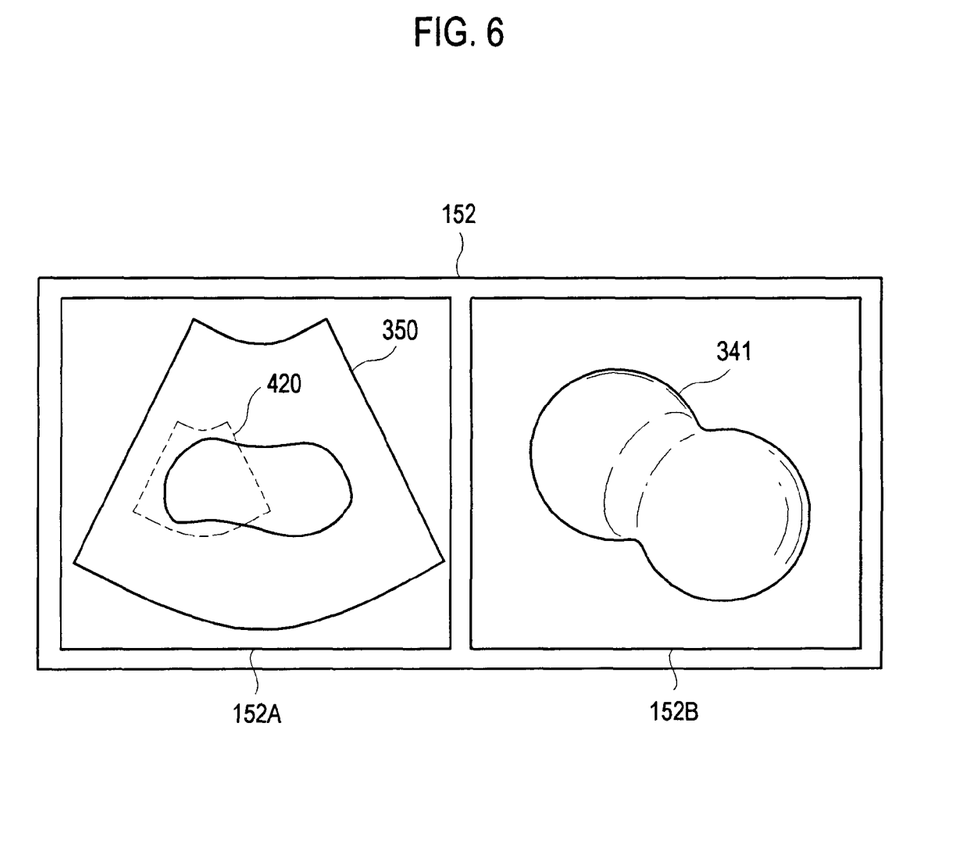

At step S108, if it is determined that the ROI setting information is inputted by the control unit 160, the processor 140 sets the ROI 320 on the reference plane image 310 based on the ROI setting information and extracts data corresponding to the ROI 320 from the volume data stored in the storage unit 130 at step S110. The processor 140 performs image signal processing based on the extracted data, thereby forming a ROI image signal and a 3D image signal corresponding to the ROI 320 at step S112. The display unit 150 receives the ROI image signal and the 3D image signal to display a ROI image 331 and a 3D image 341 on the first and second sub display regions 152A and 152B, respectively, at the same time as shown in FIG. 5 at step S 114.

Subsequently, the control unit 160 checks whether ROI reset information for resetting ROI is inputted through the input unit in real time at step S116. If the ROI reset information is not inputted, the process goes to step S126. On the other hand, if it is determined that the ROI reset information is inputted, the control unit 160 may control to the reference plane image to be displayed on the first sub display region 152A instead of displaying the ROI image at step S118. The processor 140 sets a new ROI 420 on the reference plane image displayed on the first sub display region 152A based on the ROI reset information at step S120.

Figure 7:
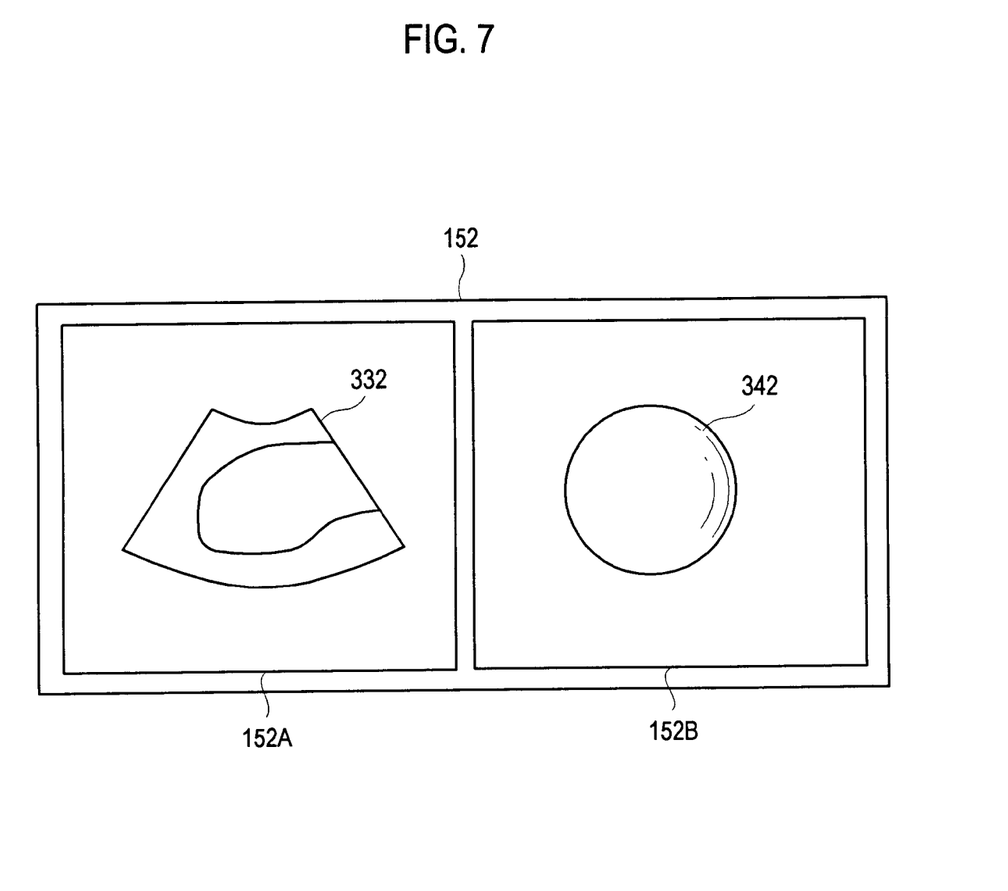

Thereafter, the steps S110 to S114 are repeated to thereby display a ROI image 332 and a 3D image 342 corresponding to the new ROI on the first and second sub display regions 152A and 152B, respectively, as shown in FIG. 7.

As mentioned above, since the ROI can be easily reset in real time without changing a display mode, the user may conveniently reset ROI and time required for diagnosis can be reduced.

In accordance with one embodiment of the present invention, there is provided an ultrasound system comprising: a diagnosis unit operable to transmit ultrasound signals to a target object and receive ultrasound signals reflected from the target object; a volume data forming unit operable to form volume data based on the received ultrasound signals; an input unit operable to receive plane selection information, region of interest (ROI) setting information and ROI reset information from a user; a processor operable to form a plane image based on plane data extracted from the volume data according to the plane selection information and set a ROI on the plane image based on the ROI setting information, said processor being configured to form a ROI image and a 3D image corresponding to the set ROI by using the volume data; a display unit operable to display at least one of the plane image or the ROI image together with the 3D image; and a control unit operable to control the display unit to display the plane image while the 3D image is displayed in response to the ROI reset information, and control the processor to set a new ROI on the displayed plane image based on the ROI reset information and form a ROI image and a 3D image corresponding to the new ROI.

In accordance with another embodiment of the present invention, there is provided a method for forming an ultrasound image, comprising: a) forming volume data based on ultrasound signals reflected from a target object; b) receiving plane selection information and forming a plane image based on plane data extracted from the volume data according to the plane selection information; c) receiving ROI setting information to set a ROI on the plane image; d) forming a ROI image and a 3-dimensional (3D) image corresponding to the ROI by using the volume data and displaying the ROI image together with the 3D image; e) receiving ROI reset information for resetting the ROI in real time; f) displaying the plane image while the 3D image is displayed in response to the ROI reset information; g) setting a new ROI on the displayed plane image based on the ROI reset information; and f) forming and displaying a ROI image and a 3D image corresponding to the new ROI.

Any reference in this specification to "one embodiment," "an embodiment," "example embodiment," etc., means that a particular feature, structure or characteristic described in connection with the embodiment is included in at least one embodiment of the invention. The appearances of such phrases in various places in the specification are not necessarily all referring to the same embodiment. Further, when a particular feature, structure or characteristic is described in connection with any embodiment, it is submitted that it is within the purview of one skilled in the art to effect such feature, structure or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An ultrasound system comprising:
a diagnosis unit configured to transmit ultrasound signals to a target object and receive ultrasound signals reflected from the target object;
a volume data forming unit configured to form volume data based on the received ultrasound signals;
an input unit configured to receive plane selection information, and region of interest (ROI) setting information from a user;
a processor configured to extract plane data from the volume data according to the plane selection information to form a plane image and set a ROI on the plane image based on the ROI setting information, said processor being configured to extract at least a portion of the volume data based on the set ROI to form a ROI image and a 3D image corresponding to the ROI image; and
a control unit operable to control a display unit to display the ROI image together with the 3D image and control the processor to set a new ROI on the displayed plane image based on updated ROI setting information received through the input unit to form a new ROI image and a 3D image corresponding to the new ROI image.

2. The ultrasound system of claim 1, further comprising a storage unit to store the volume data.

3. The ultrasound system of claim 1, wherein the input unit is a user interface configured to receive tactile input from the user.

4. The ultrasound system of claim 1, wherein the input unit is further configured to receive the updated ROI setting information when the display unit is displaying the ROI image together with the 3D image.

5. A method for forming an ultrasound image, comprising:
forming volume data based on ultrasound signals reflected from a target object;
receiving plane selection information and forming a plane image based on plane data extracted from the volume data according to the plane selection information;
receiving region of interest (ROI) setting information to set a ROI on the plane image;
extracting at least a portion of the volume data based on the set ROI to form a ROI image and a 3-dimensional (3D) image corresponding to the ROI image and displaying the ROI image together with the 3D image;
receiving updated ROI setting information for setting a new ROI in real time;
displaying the plane image together with the 3D image;
setting the new ROI on the displayed plane image based on the updated ROI setting information; and
forming and displaying a new ROI image and a 3D image corresponding to the new ROI image.

6. The method of claim 5, further comprising storing the volume data.

7. The method of claim 6, wherein, during the extracting, the ROI image is displayed on a first display region and the 3D image is displayed on a second display region, and, during the displaying the plane image together with the 3D image, the plane image is displayed on the first display region and the 3D image is displayed on the second display region.

* * * * *